US007998191B2

(12) United States Patent
Merrill et al.

(10) Patent No.: US 7,998,191 B2
(45) Date of Patent: Aug. 16, 2011

(54) APPARATUS FOR PREPARING AN ENDOLUMINAL PROSTHESES FOR LOADING INTO A DELIVERY APPARATUS

(75) Inventors: Scott Merrill, Tempe, AZ (US); Scott Pletzer, Gilbert, AZ (US)

(73) Assignee: Bard Peripheral Vascular, Inc., Tempe, AZ (US)

(*) Notice: Subject to any disclaimer, the term of this patent is extended or adjusted under 35 U.S.C. 154(b) by 1868 days.

(21) Appl. No.: 10/842,280

(22) Filed: May 10, 2004

(65) Prior Publication Data
US 2004/0207115 A1 Oct. 21, 2004

Related U.S. Application Data

(62) Division of application No. 09/826,267, filed on Apr. 4, 2001, now Pat. No. 6,756,007.

(51) Int. Cl.
*A61F 2/06* (2006.01)
(52) U.S. Cl. .......................................... 623/1.15; 72/74
(58) Field of Classification Search .................. 623/1.11, 623/1.12, 1.13, 1.15, 1.2; 29/508, 515–517; 72/80–83, 142, 370.19, 370.2, 402, 74
See application file for complete search history.

(56) References Cited

U.S. PATENT DOCUMENTS

| | | | |
|---|---|---|---|
| 3,337,673 A | 8/1967 | Jeckel | |
| 3,688,537 A * | 9/1972 | Schneider et al. | 72/74 |
| 3,998,919 A | 12/1976 | Urquhart | |
| 4,124,426 A | 11/1978 | Saul | |
| 4,427,616 A | 1/1984 | Ketcham | |
| 4,827,747 A * | 5/1989 | Okada et al. | 72/59 |
| 4,876,051 A | 10/1989 | Campbell et al. | |
| 5,282,847 A | 2/1994 | Trescony et al. | |
| 5,413,601 A | 5/1995 | Keshelava | |
| 5,476,506 A | 12/1995 | Lunn | |
| 5,512,033 A | 4/1996 | Westrum et al. | |
| 5,667,523 A | 9/1997 | Bynon et al. | |
| 5,749,880 A * | 5/1998 | Banas et al. | 606/198 |
| 5,788,626 A | 8/1998 | Thompson | |
| 5,800,522 A | 9/1998 | Campbell et al. | |
| 5,810,870 A | 9/1998 | Myers et al. | |
| 5,855,598 A * | 1/1999 | Pinchuk | 623/1.13 |

(Continued)

FOREIGN PATENT DOCUMENTS

DE 2829041 A 1/1980

(Continued)

OTHER PUBLICATIONS

Jun. 27, 2003, Search Report, PCT.

(Continued)

*Primary Examiner* — Gary Jackson
*Assistant Examiner* — Eric Blatt
(74) *Attorney, Agent, or Firm* — Rutan & Tucker, LLP

(57) ABSTRACT

An apparatus for preparing an endoluminal prostheses, having at least one layer of biocompatible material, for loading into a delivery device. The apparatus ensures the uniform collapse of the prosthesis and enables the use of diminished loading forces for loading the prosthesis into the delivery device. The apparatus includes a device to stabilize the prosthesis so that the prosthesis can be incrementally axially rotated, as well as a device to manipulate the layer of biocompatible material simultaneously at several distinct points along an axis of the prosthesis so that a set of alterations is formed in the layer of biocompatible material.

5 Claims, 5 Drawing Sheets

U.S. PATENT DOCUMENTS

| | | | |
|---|---|---|---|
| 5,897,587 A | 4/1999 | Martakos et al. | |
| 5,993,489 A | 11/1999 | Lewis et al. | |
| 6,010,529 A | 1/2000 | Herweck et al. | |
| 6,016,848 A | 1/2000 | Egres, Jr. | |
| 6,039,755 A | 3/2000 | Edwin et al. | |
| 6,053,938 A | 4/2000 | Goldmann et al. | |
| 6,077,217 A | 6/2000 | Love et al. | |
| 6,096,027 A | 8/2000 | Layne | |
| 6,139,573 A | 10/2000 | Sogard et al. | |
| 6,315,791 B1 | 11/2001 | Gingras et al. | |
| 6,508,966 B1 | 1/2003 | Castro et al. | |
| 6,510,722 B1 * | 1/2003 | Ching et al. | 72/402 |
| 6,626,938 B1 * | 9/2003 | Butaric et al. | 623/1.28 |
| 6,673,102 B1 | 1/2004 | Vonesh et al. | |
| 6,699,255 B1 * | 3/2004 | Cushchieri et al. | 606/139 |

FOREIGN PATENT DOCUMENTS

| | | |
|---|---|---|
| JP | 58131036 A | 8/1983 |
| WO | 0018328 A1 | 4/2000 |
| WO | 0019943 A1 | 4/2000 |
| WO | 0045739 A1 | 8/2000 |
| WO | 0047135 A1 | 8/2000 |

OTHER PUBLICATIONS

EP 02733916.7 filed Mar. 27, 2002 Office Action dated Feb. 17, 2011.
EP 02733916.7 filed Mar. 27, 2002 Office Action dated Oct. 1, 2008.
PCT/US2002/009874 filed Mar. 27, 2002 International Preliminary Examination Report dated Jul. 18, 2003.

* cited by examiner

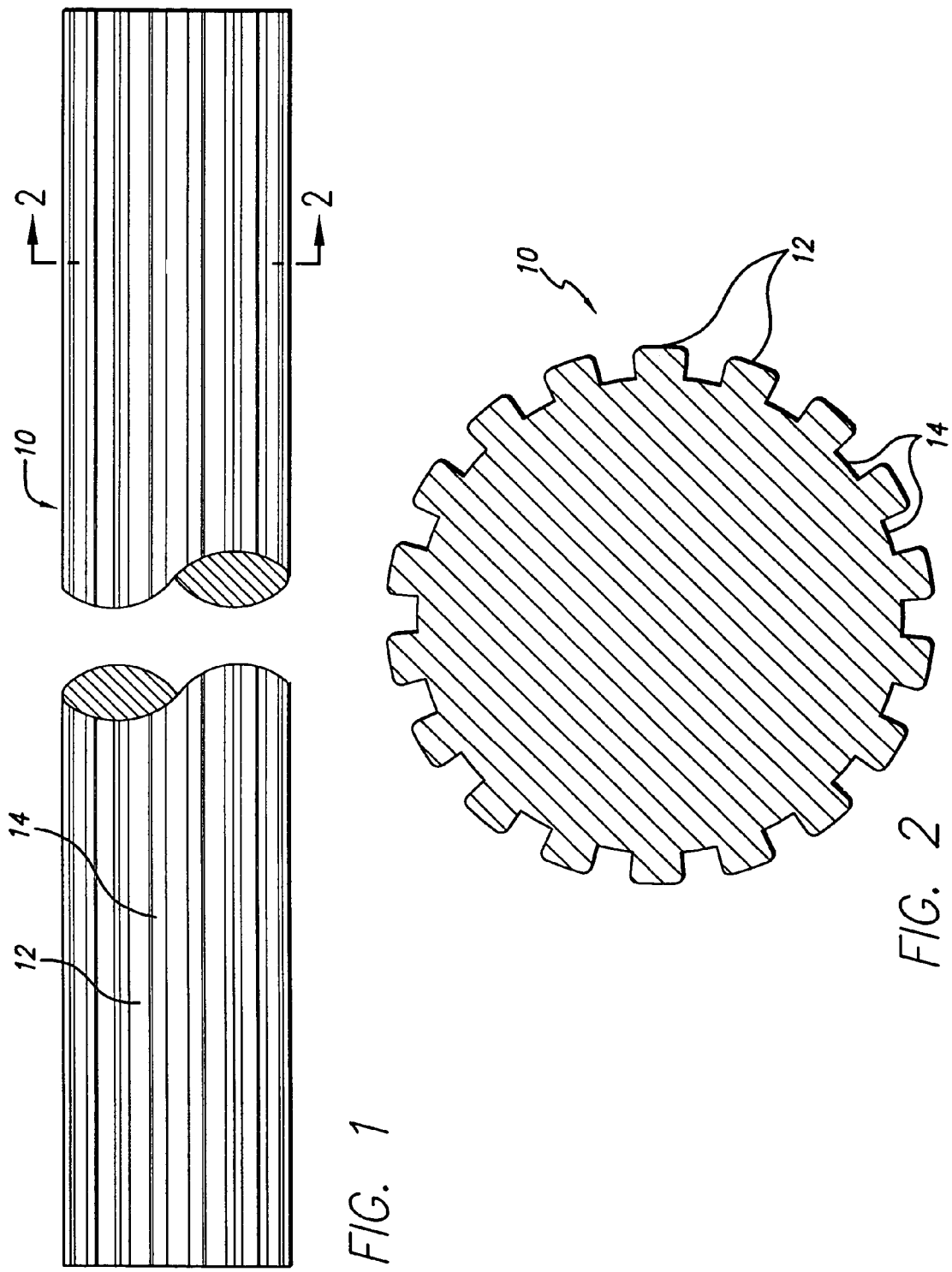

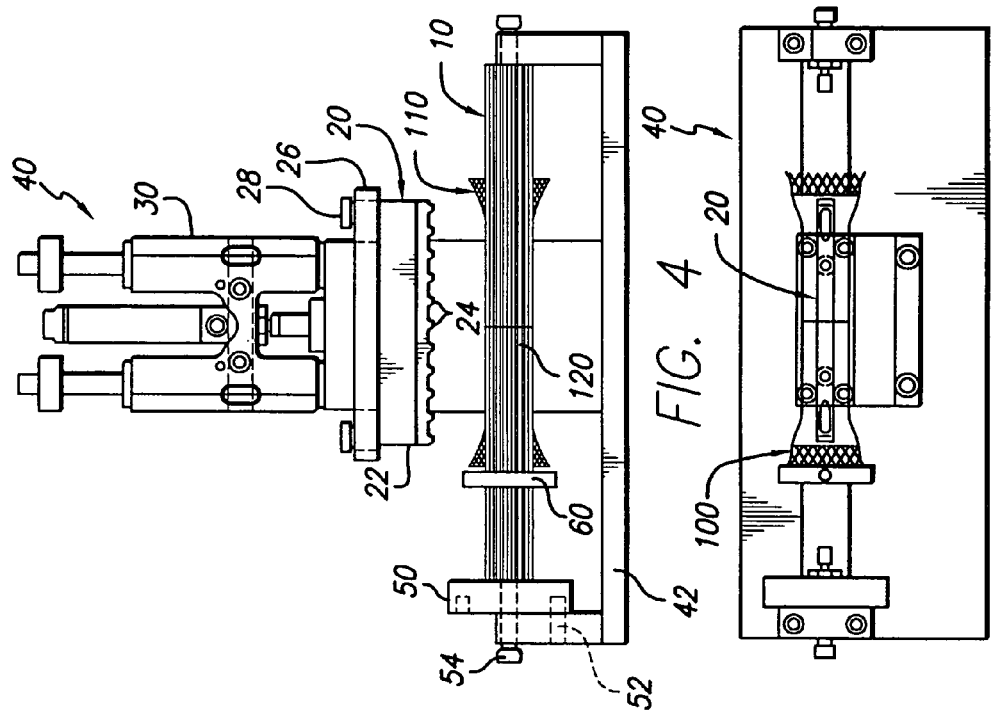
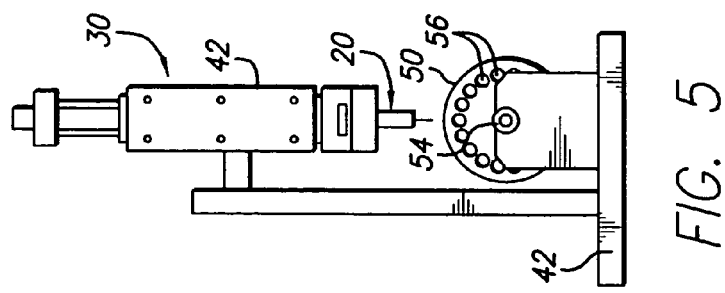

APPARATUS FOR PREPARING AN ENDOLUMINAL PROSTHESES FOR LOADING INTO A DELIVERY APPARATUS

CROSS-REFERENCE TO RELATED APPLICATIONS

This application is a division of U.S. patent application Ser. No. 09/826,267, filed Apr. 4, 2001, now U.S. Pat. No. 6,756,007, and expressly incorporates by reference the entirety thereof as if fully set forth herein.

STATEMENT REGARDING FEDERALLY SPONSORED RESEARCH OR DEVELOPMENT

Not applicable.

REFERENCE TO A COMPACT DISK APPENDIX

Not applicable.

FIELD OF THE INVENTION

The present invention relates generally to a device and method for aiding the process of loading endoluminal devices into a delivery apparatus. More particularly, the present invention is directed to a device and method to facilitate the collapse of a prosthesis.

BACKGROUND OF THE INVENTION

Endoluminal prostheses such as stents, stent-grafts and other related devices are used to treat vessels that have become weakened or diseased. These prostheses are used in a variety of circumstances to provide a remedy for the damaged vessels. The remedy can come in the form, for example, of added support for a vessel that has become weakened as a result of an aneurysm, or to reopen a vessel in which flow has been restricted due to diseases such as arteriosclerosis.

In order to effectively deliver a prosthesis to the problematic site in the vasculature of the patient, the prosthesis must first be placed within a delivery apparatus, generally including a restrictive sheath or catheter. For example, U.S. Pat. No. 6,096,027, incorporated by reference herein, describes a loading device to compress and load prostheses onto or into a catheter. This is accomplished by placing a stent device into a flexible sleeve or bag, and pulling the bagged stent device through a funnel shaped apparatus. At the end of the funnel taper, a catheter is positioned either to receive the stent device therein, or to accept the stent device thereon. The use of the bag or sleeve to pull the stent device through a funnel-shaped loading apparatus acts to minimize frictional forces inherent in collapsing a stent device from its full diameter, as well as avoiding the longitudinally applied forces associated with pushing a stent device through a loading mechanism.

The loading process described above can be additionally facilitated, particularly for large diameter stent and stent-grafts, by providing further methods to reduce the loading forces. Thus, it is desirable to provide devices and methods for preparing endoluminal prostheses in order to diminish frictional forces acting on the prostheses during the loading thereof into a delivery apparatus.

BRIEF SUMMARY OF THE INVENTION

The present invention relates to devices and methods to facilitate the loading of a prosthesis into a delivery apparatus. More particularly, the present invention is related to devices and methods for forming alterations in the prosthesis to make collapsing of the prosthesis easier by reducing frictional forces acting thereon during the process of loading the prosthesis into a delivery apparatus. Advantageously, creation of alterations in the prosthesis enables a more compact collapse, leading to a smaller insertion profile. This is beneficial to both the physician and patient as complications inherent with the insertion of prostheses are largely reduced.

In preferred embodiments of the present invention, a device to create alterations in a prosthesis includes a grooved mandrel and a pressing comb. The grooved mandrel is preferably a tubular object made from a hard substance, such as stainless steel, with grooves running longitudinally down its length. The grooves are spaced around the circumference of the mandrel, creating two distinct diameters, one for the grooved areas and another for the non-grooved or raised areas. Such a device is also known as a "splined" mandrel to those of skill in the art. The pressing comb is preferably a long hard structure also preferably made of stainless steel, having teeth to create an alteration in a prosthesis without puncturing a layer thereof. The teeth of the comb are therefore extremely short in comparison to a conventional comb. One preferred embodiment of this device additionally includes a coupling apparatus, which not only connects the mandrel and the comb, but also coordinates their actions with respect to one another, mechanically controlling the alteration process.

In a preferred method of utilizing the above-described embodiment of the present invention, the grooved mandrel is placed into the prosthesis, preferably such that a tight fit between the two is achieved, and mounted on a receiving rack. The receiving rack is attached to the coupling apparatus, which is in turn attached to the pressing comb. When the coupling apparatus is activated (i.e., by using a pneumatic control box), the pressing comb is moved a pre-determined distance downward, making contact with the prosthesis (the underlying mandrel being positioned such that a grooved section is facing the comb), until a longitudinal set of alterations is created. The mandrel is then axially rotated until the adjacent grooved section is facing upward and another set of alterations is fashioned. This process is continued until a desired number of sets of alterations are produced.

In other preferred embodiments of the present invention, a device to create alterations in a prosthesis includes a grooved mandrel, a marking wheel and a shaft. The marking wheel can have teeth spaced around its circumference to effectuate an alteration on a prosthesis when the wheel runs along its periphery. In practice, the grooved mandrel is placed within the prosthesis and the shaft is placed through the middle of the marking wheel. The shaft is then used to move the wheel longitudinally down the outside of the prosthesis, forming alterations thereon. Of course, as in the embodiment described above, it would be advantageous to utilize a coupling apparatus to coordinate the formation of the alterations on the desired portion of the prosthesis.

These and other features and advantages of the present invention will become more apparent to those skilled in the art when taken with reference to the following more detailed description of the preferred embodiments of the invention and the accompanying drawings.

BRIEF SUMMARY OF THE DRAWINGS

FIG. 1 depicts a longitudinal view of a grooved mandrel of the present invention.

FIG. 2 depicts a cross-sectional view of a grooved mandrel of the present invention.

FIG. 4 depicts a frontal view of a preferred embodiment of the present invention, showing a fully assembled pressed comb apparatus.

FIG. 5 depicts a side view of FIG. 4.

FIG. 6 depicts an overhead view of FIG. 4.

DETAILED DESCRIPTION OF THE INVENTION

Turning now to the drawings, the present invention relates to devices and methods used to create alterations in a layer of biocompatible material covering or encapsulating a stent. The preferred biocompatible material utilized to cover and encapsulate stents for the present invention is expanded polytetrafluoroethylene (ePTFE), although a number of different materials are certainly within the scope of this invention, including polytetrafluoroethylene, polyesters, polyurethanes and other covering materials that would be, at a minimum, temporarily deformed from an alteration process such as the one described in the present invention. The term alteration as used herein means a small indentation, crease, dimple or differential density created in the surface of the ePTFE or other biocompatible material.

Referring to FIGS. 1 and 2, a grooved mandrel 10 is illustrated. Grooved mandrel 10 is tubular with two distinct diameters, which successively alternate about its circumference. This can best be seen in the cross-sectional view of FIG. 2, where each grooved section 14 set at a first diameter is immediately followed by a raised section 12 set at a second diameter. The importance of the two distinct sections 12 and 14 on the grooved mandrel 10 will be appreciated to one of skill in the art with respect to the creation of the alterations in the covered stents, described in more detail below.

Figure 3:
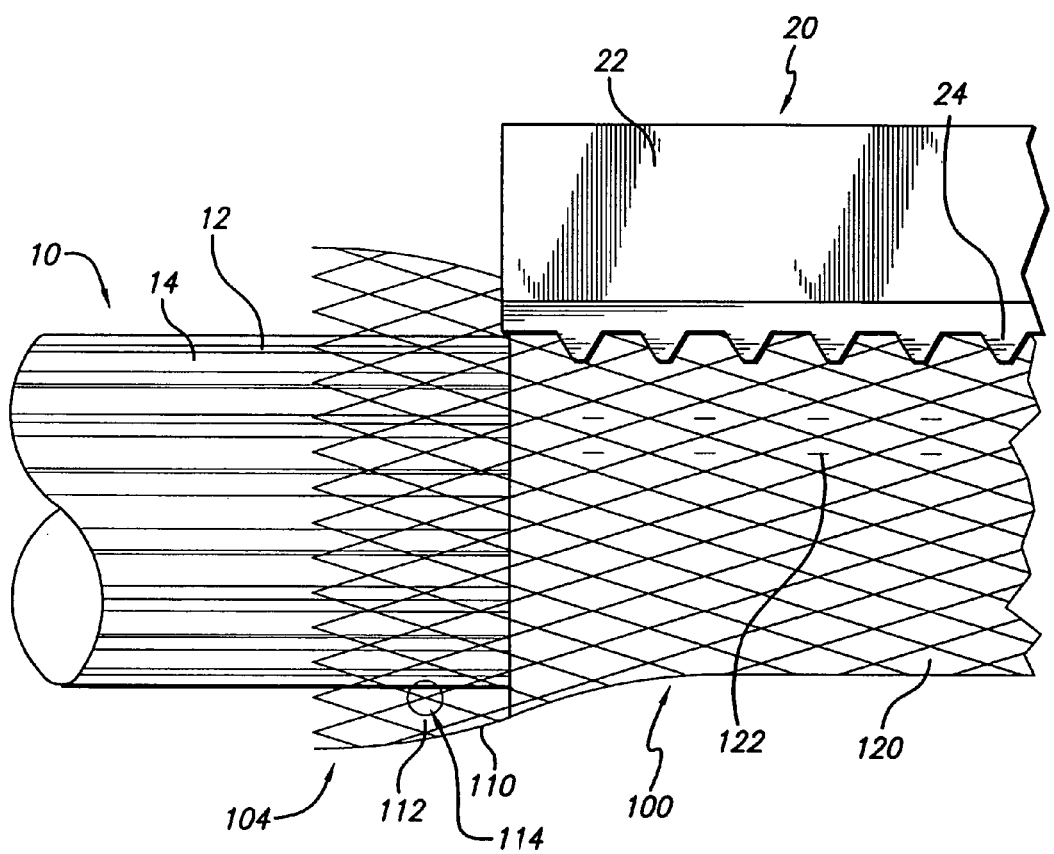
FIG. 3 depicts a close-up view of a pressed comb of the present invention acting on an esophageal stent with a grooved mandrel inserted therethrough.

FIG. 3 illustrates a close-up view of the creation of alterations 122 in the ePTFE covering 120 of an esophageal stent-graft 100. The esophageal stent-graft 100 has a stent 110 that is encapsulated by an ePTFE covering 120. The term encapsulated as used herein means at least one layer of biocompatible material, in this case ePTFE, covering each of the luminal and abluminal layers of the stent and adhered to one another through the walls of the stent. Ends 104 of the esophageal stent-graft 100 can be left uncovered and flared outward from a central axis of the stent 100 as shown. In a preferred embodiment of the present invention, the esophageal stent-graft 100 is mounted on the grooved mandrel 10 (see FIGS. 4-6 for more detail). Pressing comb 20 is positioned to contact the ePTFE covering 120 of the esophageal stent-graft 100 at measured equidistant intervals longitudinally along the length of the stent-graft 100. The grooved mandrel 10 is positioned within the stent-graft 100 such that the grooves 12 of the mandrel 10 are underneath each set of alterations to be fashioned. When contact is made between teeth 24 of the pressing comb 20 and the ePTFE covering 120 at each groove 12 of the mandrel 10, an alteration 122 is created in the ePTFE covering 120.

The devices and methods to create alterations in biocompatible layers according to the present invention are especially advantageous to large diameter prostheses such as the esophageal stent-graft 100 illustrated herein. This is due to the presence of increased loading forces acting on a larger diameter prosthesis (compared to a smaller diameter prosthesis) when collapsing for loading into a delivery apparatus. However, it should be appreciated that the devices and methods presented herein are equally applicable to biliary stents and other small diameter covered stents as well as grafts or sheaths or other endoluminal prostheses. Moreover, the present invention can be used for purposes unrelated to implantable prostheses where alteration techniques can be used advantageously; for example, where such manipulation of the surface of a material provides increased or facilitated performance of the material or apparatus with which the material is attached or associated in some capacity.

Ideally, the alterations 122 will be created in the ePTFE covering 120 at a mid-point 112 between successive longitudinal articulations 114 in the stent 110. The term articulation as used herein means a tip or point of a diamond shape in the stent wall. The creation of an alteration 122 at the mid-point 112 between successive longitudinal articulations 114 is accomplished through spacing of the teeth 24 of comb 20 and pre-positioning of the comb 20 prior to the creation of the alterations 122 in accordance with the articulation 114 spacing, so that the teeth 24 correspond to the mid-points 112. When the comb 20 comes into contact with the ePTFE covering 120, a set of alterations 122 will simultaneously be produced along a longitudinal axis of the esophageal stent-graft 100.

Turning now to FIGS. 4-6, a preferred embodiment of the present invention is illustrated. FIG. 4 shows a front view of a pressing comb device 40 with esophageal stent-graft 100 mounted thereon. As partially shown in FIG. 3, the grooved mandrel 10 is inserted through the center of esophageal stent-graft 100. This enables the mounting and stabilization of the esophageal stent-graft 100 for creation of alterations 122 in the ePTFE covering 120. The mandrel 10 is coupled to a main support structure 42 by support pins 54, which are inserted into the center of the mandrel 10 whereby the mandrel 10 with the esophageal stent-graft 100 mounted is fully rotatable. A stop disk 60 abuts one end of the esophageal stent-graft 100 to prevent the esophageal stent-graft 100 from migrating, and a detent disk 50 is coupled to the mandrel 10 via one of the pins 54 to control the rotation of the esophageal stent-graft 100. The control of the esophageal stent-graft 100 is further accomplished through the use of a locking pin 52, which is utilized to lock the detent disk 50 in each axial position for creation of alterations on the esophageal stent-graft 100. The locking action of pin 52 can best be seen in FIG. 5, where an end view of the pressing comb device 40 is shown. The detent disk 50 has several pin holes 56 therein, each associated with an axial position of the esophageal stent-graft 100 where a set of alterations is desired. Certainly, depending on the prosthesis or material to be manipulated by the pressing comb device 40, these pin holes 56 can be more or less numerous.

A linear slide 30 is mounted atop the main support 42. The linear slide 30 is controlled mechanically to move in a vertical direction a desired predetermined distance. Pressing comb 20 is attached to the base of the linear slide 30 via screws 28 that slide into a pressing comb body 22 through a comb mounting plate 26. The features of the pressing comb device 40 can alternatively be viewed from above in FIG. 6. From this overhead view the esophageal stent-graft 100 can be seen more clearly. Once completely mounted on the pressing comb device 40, the esophageal stent-graft 100 can be acted on by the pressing comb 20, where each pass of the pressing comb 20 downward, contacting the esophageal stent-graft 100, creates a longitudinal set of alterations 122 along the ePTFE covering 120 of the esophageal stent 100.

Figure 7:
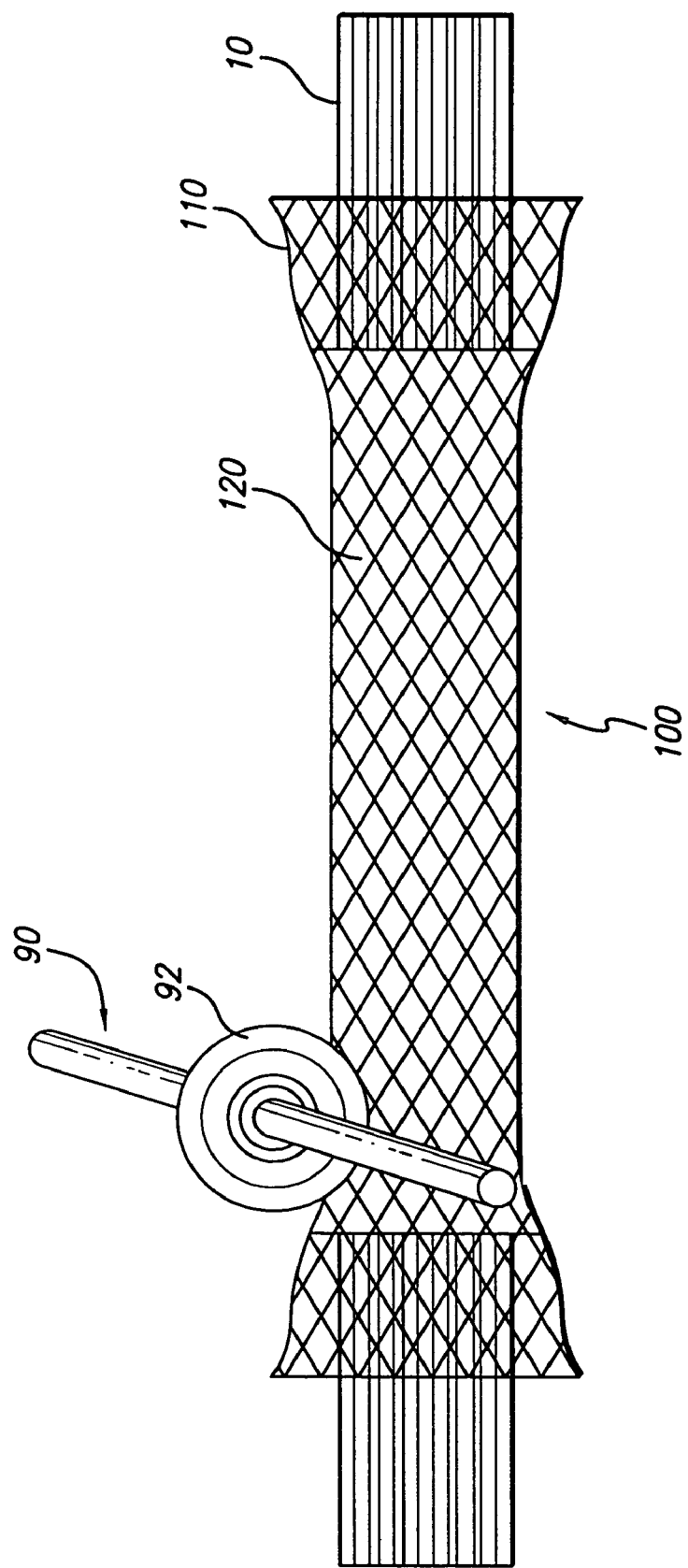
FIG. 7 depicts a marking wheel of the present invention acting on an esophageal stent.

Referring now to FIG. 7, an alternate preferred embodiment is depicted. In this embodiment, the alterations are created in the ePTFE covering 120 of the esophageal stent-graft 100 through the use of a marking wheel device 90. The marking wheel device 90 includes a marking wheel 92 and a shaft 96. The shaft 96 is positioned through the center of the marking wheel 92 for smooth and steady movement thereof. The marking wheel device 90 may have teeth around the circumference of the marking wheel 92 to produce alternating dimples in the ePTFE covering 120. In the absence of teeth, alterations can be formed by the wheel 92 itself in the form of grooves along the length of the ePTFE covering 120. In preferred embodiments, a coupling apparatus will be attached to the shaft 96 to ensure uniform movement and pressure of the wheel 92 along the ePTFE covering 120.

Figure 8:
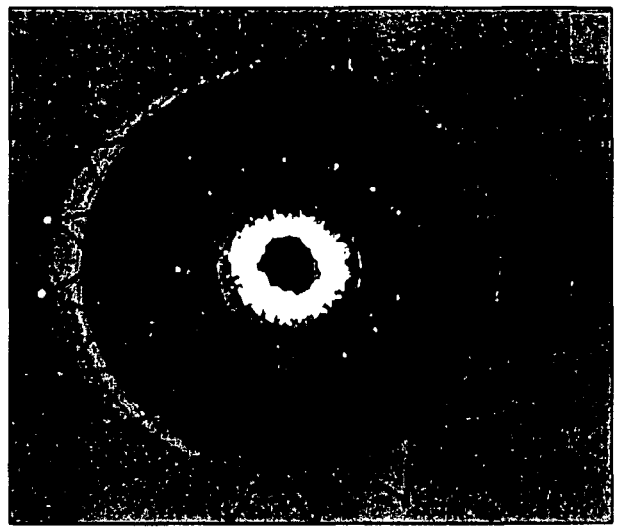
FIG. 8 is a microphotograph of an esophageal stent-graft taken from one end, prior to collapse thereof for loading into a delivery apparatus.
Figure 9:
FIG. 9 is a microphotograph of an esophageal stent-graft taken from one end following collapse thereof, without having first been altered according to the present invention.
Figure 10:
FIG. 10 is a microphotograph of an esophageal stent-graft taken from one end following collapse thereof, having first been altered according to the present invention.

FIGS. 8-10 are microphotographs of an esophageal stent-graft taken from one end, to illustrate the advantage provided by the alteration process of the present invention. FIG. 8 shows a covered esophageal stent-graft prior to collapse thereof for loading into a delivery apparatus. FIG. 9 is a microphotograph of an esophageal stent-graft following collapse thereof, without having first undergone alteration, while FIG. 10 is a microphotograph of an esophageal stent-graft following collapse thereof, having first been altered according to the present invention. It is apparent from the microphotographs that the covering of the altered stent-graft in FIG. 10 collapses in a much more uniform and compact manner than does the covering of the unaltered stent-graft in FIG. 9. As stated above, this uniform and compact collapse is advantageous for a number of reasons, including providing a smaller resultant profile for the stent-graft, which leads to a reduction in complications in the delivery process.

In alternate preferred embodiments of the present invention, rather than a set of alterations being created along a longitudinal axis of a prosthesis as described above, different sets of alterations or a series of single alterations could be produced. For example, a circumferential set of alterations could be produced along a circumferential axis of the prosthesis by a disc-like device fashioned to fit around the circumference of the prosthesis. Teeth or other alteration-forming units could be on the inside of the disc-like device and the disc could contract at once or in intervals to cause alterations on the outside of the prosthesis. Similarly, the teeth on the disc-like device could be placed around the outside of the disc, similar to the marking wheel 92 in FIG. 7, and the device could be placed within the prosthesis to be expanded outward to cause alterations on the inside of the prosthesis along a circumferential axis. In addition, circumferential alterations and longitudinal alterations could be made in concert by different types of devices, or sets of alterations could be made on different axes simultaneously.

It should also be noted that while examples have been provided herein with regard to collapse of prostheses from a large to a small diameter, the scope of the present invention extends to the creation of alterations in the prosthesis to effectuate other forms of collapse as well. Thus, for example, alterations could be produced in a prosthesis to facilitate an accordion-like collapse thereof.

Finally, many modifications may be made by those having ordinary skill in the art without departing from the scope of the present invention. In particular, it should be understood that the invention can be carried out by specifically different equipment and devices, and that various modifications, both as to the equipment details and procedures, can be accomplished without departing from the spirit and scope of the invention. The spirit and the scope of the claims should not, therefore, be limited to the description of the preferred embodiments contained herein.

What is claimed as new and desired to be protected by Letters Patent of the United States is:

1. An apparatus for preparing an endoluminal prostheses for loading into a delivery device, wherein said prosthesis comprises at least one layer of biocompatible material, comprising:
   a stabilization device configured for insertion within a lumen of said endoluminal prosthesis, comprising a grooved mandrel with a plurality of longitudinal grooves around the circumference thereof;
   an alteration device comprising spaced apart teeth configured for creating alterations in a surface of said layer of biocompatible material; and
   a support device coupled to said alteration device, said support device being adapted to move said alteration device into selective contact with said endoluminal prosthesis, said support device coupled to said mandrel via support pins inserted into opposing ends of said mandrel, wherein said support device is adapted to rotate said mandrel, said support device further comprising a stop disk positioned adjacent one of said opposing ends of said mandrel.

2. The apparatus according to claim 1, further comprising a detent disk and a locking pin that cooperate to position and hold said mandrel at a plurality of axial positions.

3. The apparatus according to claim 2, wherein said alteration device comprises a pressing comb, further comprising a linear slide attached to said pressing comb, wherein said linear slide is adapted to move said pressing comb in a vertical direction.

4. The apparatus according to claim 1, wherein said teeth on said alteration device are positioned around an inner surface thereof, said inner surface being positioned around an outer surface of said prosthesis.

5. An apparatus for preparing an endoluminal prostheses for loading into a delivery device, comprising:
   a stabilization device configured for insertion within a lumen of a stent encapsulated by a covering of expanded polytetrafluoroethylene, the stabilization device comprising a grooved mandrel with a plurality of longitudinal grooves around the circumference thereof;
   an alteration device comprising spaced apart teeth configured for creating alterations in a surface of the covering; and
   a support device coupled to the alteration device, the support device including a linear slide mechanically controlled to move said alteration device into selective contact with the covering, the support device coupled to the mandrel via support pins inserted into opposing ends of the mandrel such that the support device is adapted to rotate the mandrel, the support device including a stop disk positioned adjacent one of the opposing ends of the mandrel.

* * * * *